United States Patent
Sugiura et al.

(10) Patent No.: US 7,275,829 B2
(45) Date of Patent: Oct. 2, 2007

(54) OPHTHALMIC LASER IRRADIATION APPARATUS

(75) Inventors: Motohiro Sugiura, Gamagori (JP); Masaki Tanaka, Okazuki (JP)

(73) Assignee: Nidek Co. Ltd. (JP)

( * ) Notice: Subject to any disclaimer, the term of this patent is extended or adjusted under 35 U.S.C. 154(b) by 608 days.

(21) Appl. No.: 10/855,422

(22) Filed: May 28, 2004

(65) Prior Publication Data

US 2004/0243113 A1  Dec. 2, 2004

(30) Foreign Application Priority Data

May 30, 2003  (JP) .............................. 2003-155801

(51) Int. Cl.
*A61B 3/10*  (2006.01)
(52) U.S. Cl. ...................................... 351/221
(58) Field of Classification Search ................ 351/221, 351/204, 206
See application file for complete search history.

(56) References Cited

U.S. PATENT DOCUMENTS

| | | | |
|---|---|---|---|
| 5,632,742 A | 5/1997 | Frey et al. | |
| 6,159,202 A | 12/2000 | Sumiya et al. | |
| 6,283,954 B1 | 9/2001 | Yee | |
| 6,491,687 B1 | 12/2002 | Sumiya et al. | |

FOREIGN PATENT DOCUMENTS

WO  WO 01/28476 A1  4/2001

*Primary Examiner*—Alicia M Harrington
(74) *Attorney, Agent, or Firm*—Rader Fishman & Grauer PLLC; Ronald P. Kananen

(57) ABSTRACT

An ophthalmic laser irradiation apparatus for irradiating a laser beam onto a patient's eye capable of preventing a deviation of an irradiation position of the laser beam due to a change in a pupil (iris), and performing laser irradiation within high precision. The apparatus has an irradiation optical system for irradiating the laser beam onto the eye, an illumination unit, including an illumination light source, in which light intensity of visible illumination light onto the eye is adjustable, a detection unit which detects at least one of a pupil area and a pupil diameter of the eye, a setting unit which sets a reference value of at least one of the pupil area and the pupil diameter, and an informing unit which informs at least one of a detection value of the detection unit along with the set reference value and a comparison result thereof.

8 Claims, 5 Drawing Sheets

OPHTHALMIC LASER IRRADIATION APPARATUS

BACKGROUND OF THE INVENTION

1. Field of the Invention

The present invention relates to an ophthalmic laser irradiation apparatus for irradiating a laser beam onto a patient's eye.

2. Description of Related Art

As an ophthalmic laser irradiation apparatus for irradiating a laser beam onto a patient's eye, for example, there is a corneal laser surgery apparatus which ablates a corneal tissue by irradiating an excimer laser beam and changes corneal curvature to correct a refractive error of the eye. In addition, as the ophthalmic laser irradiation apparatus, there is an apparatus provided with an alignment mechanism for aligning an irradiation position of the laser beam (hereinafter, also simply referred to as an "irradiation position") with reference to a predetermined position of the eye, and further provided with a tracking mechanism for aligning (moving) the irradiation position even if the eye (an eyeball) moves during operation. Further, as an apparatus provided with those alignment mechanism and tracking mechanism, such an apparatus is proposed that determines the irradiation position with reference to a position (part) relating to a pupil (including an iris which forms the pupil) such as a pupil center position.

The pupil (iris), however, changes (dilates, contracts, and the like) depending on brightness. Further, due to the charge in the pupil (iris), also various positions (parts) such as the pupil center position change (deviate) Therefore, in a case where the irradiation position is determined with reference to the position (part) relating to the pupil (iris), if the pupil (iris) changes, the irradiation position is misaligned, and it causes an error in a post-operative correction result.

SUMMARY OF THE INVENTION

The present invention has been made in view of the above circumstances and an object to overcome the above problems and to provide an ophthalmic laser irradiation apparatus capable of preventing a deviation of an irradiation position of a laser beam due to a change in a pupil (iris), and performing laser irradiation with high precision.

To achieve the objects and in accordance with the purpose of the present invention, an ophthalmic laser irradiation apparatus is provided with an irradiation optical system for irradiating a laser beam onto a patient's eye, an illumination unit, including an illumination light source, in which light intensity of visible illumination light onto the eye is adjustable, a detection unit which detects at least one of a pupil area and a pupil diameter of the eye, a setting unit which sets a reference value of at least one of the pupil area and the pupil diameter, and an informing unit which informs at least one of a detection value of the detection unit along with the set reference value and a comparison result thereof.

In another aspect of the present invention, an ophthalmic laser irradiation apparatus is provided with an irradiation optical system for irradiating a laser bean onto a patient's eye, an illumination unit, including an illumination light source, in which light intensity of visible illumination light onto the eye is adjustable, a detection unit which detects at least one of a pupil area and a pupil diameter of the eye, a setting unit which sets a reference value of at least one of the pupil area and the pupil diameter, and a control unit which controls the illumination unit to adjust the light intensity of the visible illumination light so that a detection value of the detection unit becomes the set reference value.

In another aspect of the present invention, an ophthalmic laser irradiation apparatus is provided with an irradiation optical system for irradiating a laser beam onto a patient's eye, an illumination unit, including an illumination light source, in which light intensity of visible illumination light onto the eye is adjustable, a detection unit which detects at least one of a pupil area and a pupil diameter of the eye, a setting unit which sets a reference value of at least one of the pupil area and the pupil diameter, and a control unit which judges whether a detection value of the detection unit becomes the set reference value and controls laser irradiation based on a judgment result.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
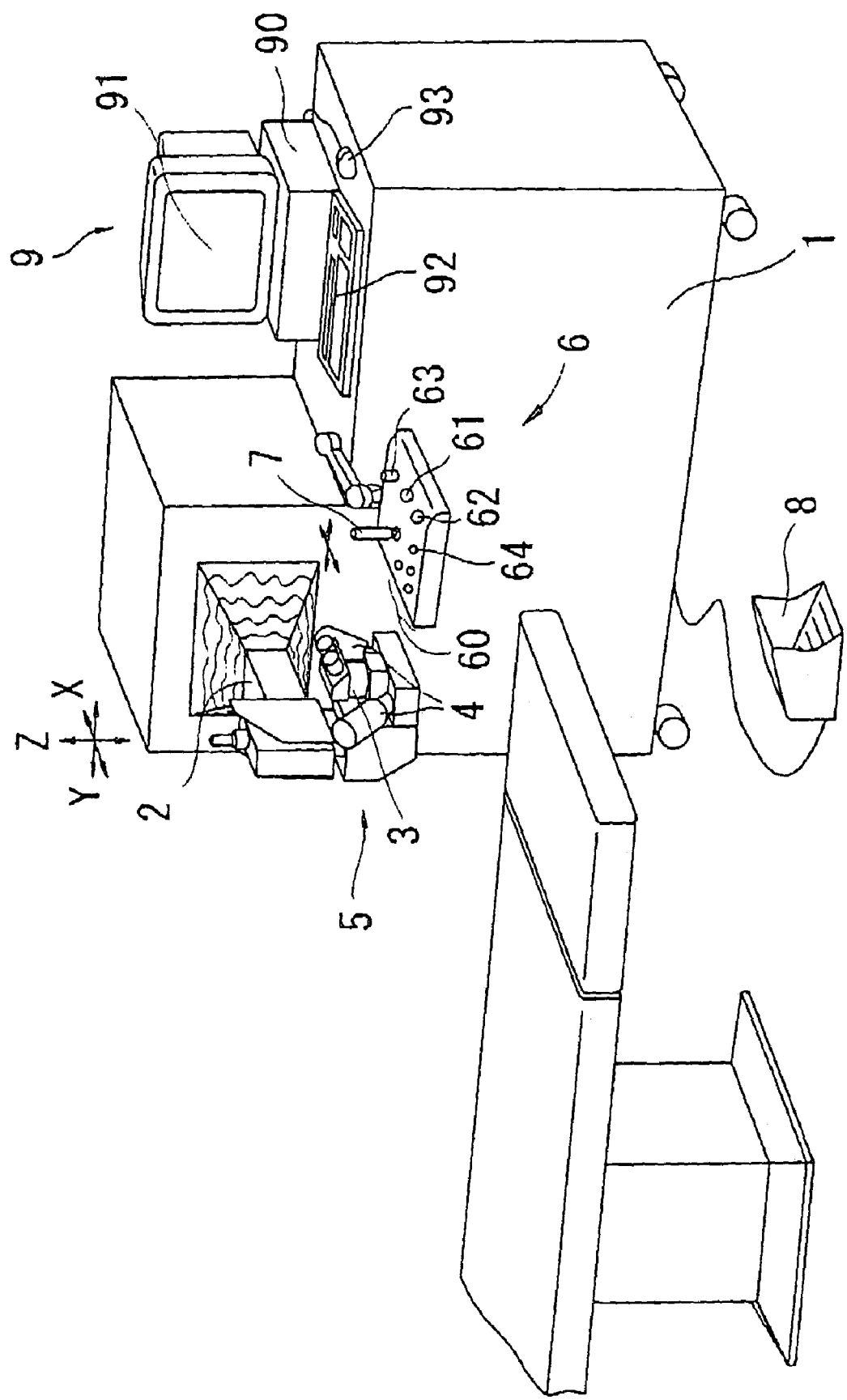
FIG. 1 is an external view of a corneal laser surgery apparatus consistent with the preferred embodiment of the present invention.
Figure 2:
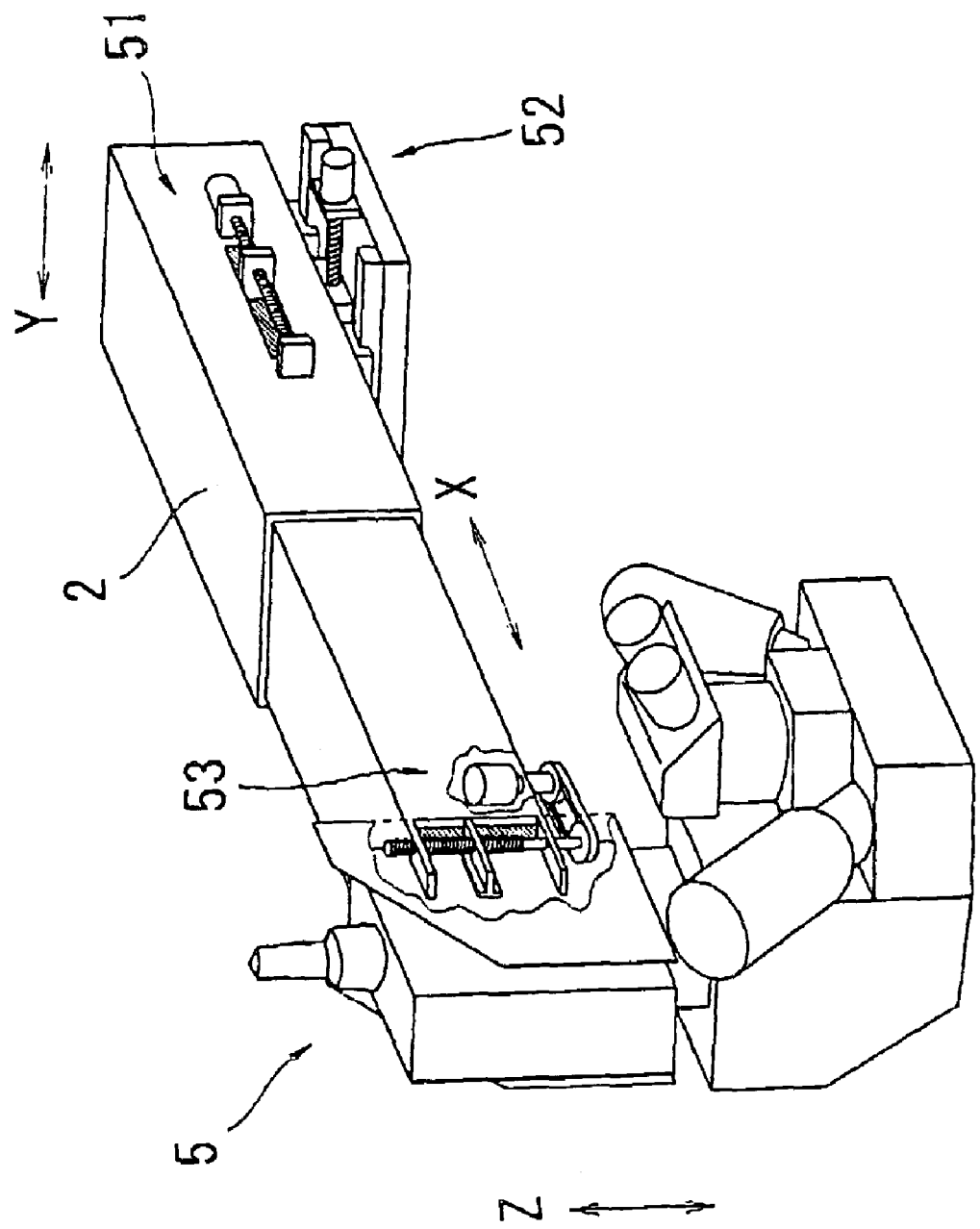
FIG. 2 is a view illustrating respective driving units in the present apparatus.
Figure 3:
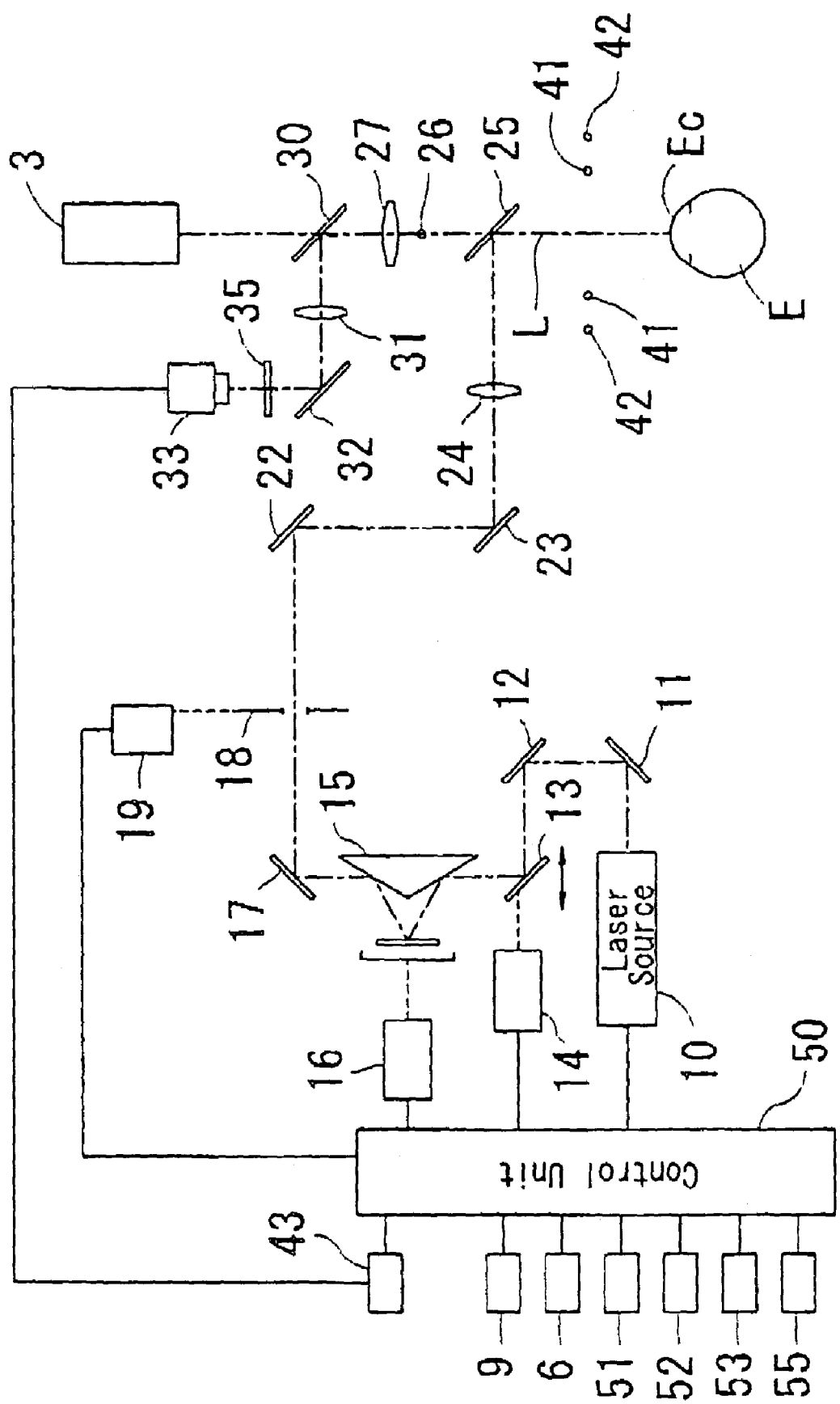
FIG. 3 is a schematic configuration of an optical system and a control system in the present apparatus.

A detailed description of one preferred embodiment of an ophthalmic laser irradiation apparatus consistent with the present invention is provided below with reference to the accompanying drawings. FIG. 1 is an external view of a corneas laser surgery apparatus. FIG. 2 is a view illustrating respective driving units in the present apparatus. FIG. 3 is a schematic configuration of an optical system and a control system in the present apparatus.

An excimer laser source 10 and the like are included in a main body 1 of the surgery apparatus. An excimer laser beam emitted from the laser source 10 is directed to an arm unit 2. An observation optical unit 5 disposed on a tip portion of the arm unit 2 is provided with a binocular microscope unit 3 for observing a patient's eye E, an illumination unit 4, an eyeball position detection system, and the like. The illumination unit 4 includes a visible illumination light source 41 which emits visible light and an infrared illumination light source 42 which emits infrared light. The light source 41 is made so that illumination light intensity is adjustable to change a pupil (iris) of the eye E.

The laser beam directed to the arm unit 2 is directed to the eye E by optical elements (described below) such as mirrors disposed inside. The arm unit 2 is moved in an X-direction (in a right-and-left direction to an operator) by an X-direction arm driving unit 51, and in a Y-direction (in a back-and-forth direction to the operator) by a Y-direction arm driving unit 52, respectively. In addition, the observation optical unit 5 is moved in a Z-direction (in a direction of a laser irradiation optical axis) by a Z-direction driving unit 53. Each of the driving units 51, 52 and 53 consists of a motor, a sliding mechanism, and the like.

A controller 6 is provided with a joystick 7 for giving a signal to move the arm unit 2 in the X- and Y-directions, a switch 60 for performing alignment in the Z-direction, a switch 61 for performing ON/CFF switching for automatic alignment, a switch 62 for switching over from a standby state to a ready (ready for laser irradiation) state, a switch 63 for adjusting the illumination light intensity of the light source 41, a switch 64 for switching over an automatic mode/a manual mode for the light intensity adjustment of the light source 41, and the like. A foot switch 8 transmits (inputs) a trigger signal for laser emission. A computer 9, consisting of a main body 90, a monitor 91, a keyboard 92, a mouse 93 and the like, inputs various data such as a necessary surgical condition, and performs calculation, display and storing of laser irradiation control data.

Irradiation Optical System

The laser beam emitted from the laser source 10 is reflected by mirrors 11 and 12, and further reflected by a plane mirror 13. The mirror 13 is moved by a driving unit 14 in the direction of the arrow indicated in FIG. 3. An image rotator 15 is rotatably driven by a driving unit 16 about a central optical axis as the center, and rotates the laser beam about the optical axis. A variable circular aperture unit 18, an opening diameter of which is varied by a driving unit 19, limits an ablation region. Mirrors 17, 22 and 23 change the direction of the laser beam. A projecting lens 24 projects the opening of the aperture unit 16 onto the cornea Ec of the eye E.

A dichroic mirror 25 has a property of reflecting the excimer laser bean of 193 nm and transmitting the visible light and the infrared light. The laser beam passed through the projecting lens 24 is reflected by the dichroic mirror 25 to be directed to the cornea Ec. L indicates a reference optical axis for the laser irradiation.

Observation System

Above the dichroic mirror 25, arranged are a visible fixation lamp 26, an objective lens 27, a dichroic mirror 30 having a property of reflecting the infrared light and transmitting the visible light, and the microscope unit 3. The operator observes an anterior-segment of the eye E illuminated by the light source 41 through the microscope unit 3.

Eyeball Position Detection System

An image forming lens 31, a mirror 32, an infrared transmission filter 35 and a CCD camera 33 are arranged sequentially on an optical path on a reflecting side of the dichroic mirror 30. An image of the anterior-segment of the eye E illuminated by the light source 42 is picked up by the CCD camera 33. An output signal from the CCD camera 33 is inputted into an image processing unit 43. An eyeball position detection system is shared as a pupil diameter detection system.

Control System

A control unit 50 for controlling the entire apparatus is connected with the laser source 10, the controller 6, the computer 9, an alarm 55, and the respective driving units 51, 52 and 53. In addition, the output signal from the CCD camera 33 is inputted into the image processing unit 43, and processed information from the image processing unit 43 is inputted into the control unit 50. The control unit 50 controls to detect a pupil position (eyeball position) and a pupil diameter based on the signal detected by the image processing unit 43, and controls the respective driving units 51, 52 and 53, and the light source 41.

Figure 4:
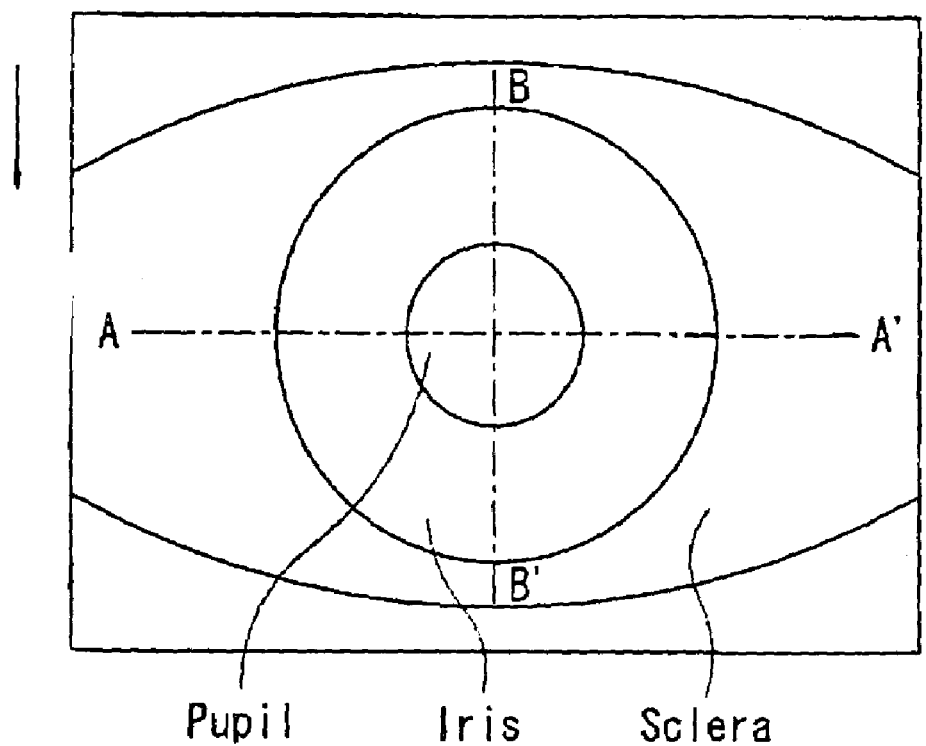
FIG. 4 is a view showing an image of an anterior-segment of an eye picked up by a CCD camera.
Figure 5:
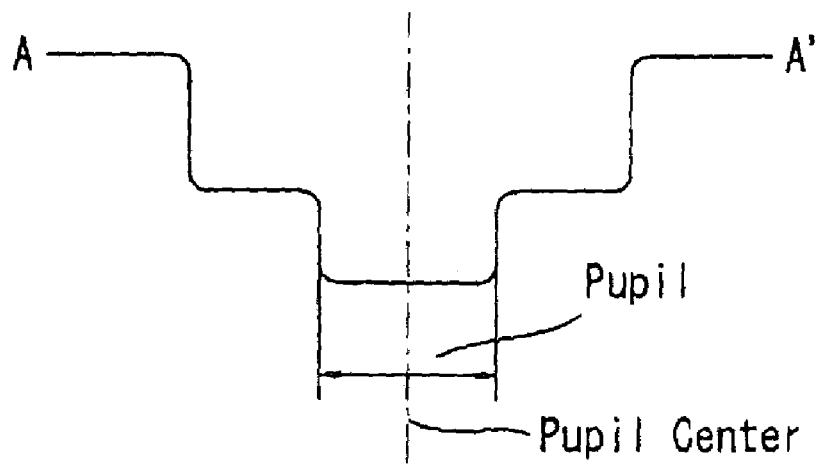
FIG. 5 is a view showing distribution of light intensity on the line A-A' in FIG. 4.

One example of methods of detecting the pupil position and the pupil diameter will be hereinafter described. FIG. 4 is a view showing the image of the anterior-segment picked up by the CCD camera 33, and FIG. 5 is a view showing distribution of light intensity on the line A-A' in FIG. 4. As shown in via 5, since the light intensity at the pupil, the iris and a sclera is different, positions (coordinates) of a pupil edge in a lateral direction may be detected from distribution information on the light intensity on the line A-A', and its center position (coordinates) maybe further detected from the positions of the pupil edge. In the same way as is described, positions (coordinates) of the pupil edge in a vertical direction may be detected from distribution information on the light intensity on the line B-B', and its center position (coordinates) may be further detected. Then, from both the center positions, a pupil center position (coordinates) is obtained with reference to a position of an optical axis of the detection system (i.e., the reference optical axis L of the irradiation optical system), which is adjusted to have a predetermined positional relationship on an image-pickup element of the CCD camera 33. Incidentally, concerning the lines for detection in the lateral and vertical directions, it is preferable that the distribution information on the light intensity on a plurality of lines are obtained while taking the center of the image-pickup element of the CCD camera 33 as the center, and averaged. In addition, when the processing time permits, a position of a barycenter of a pupil region may be obtained to be defined as the pupil center position.

Incidentally, the pupil diameter, for example, may be obtained as a distance between the positions of the leftmost edge and the rightmost edge among the positions of the pupil edge detected as above. Alternatively, it may be obtained as a distance between the positions of the uppermost edge and the lowermost edge. In addition, an area of the pupil region may be obtained from the distribution of the light intensity on the eye E.

Figure 6:
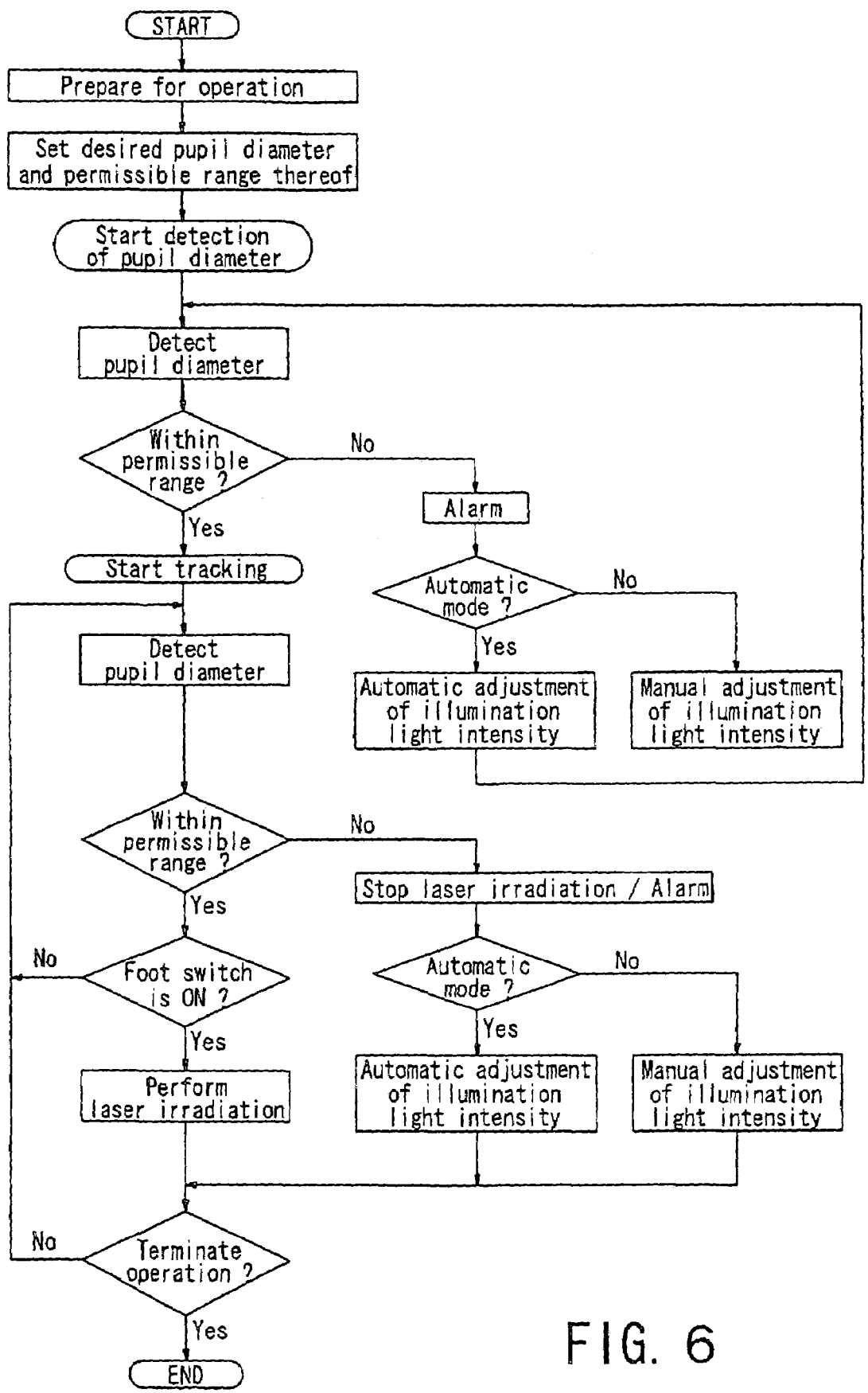
FIG. 6 is a flow chart describing operation of the present apparatus.

Next, in the apparatus having the constitution as above, its operation will be described using a flow chart in FIG. 6. The operator inputs various data such as a correction amount of the eye E previously obtained and the surgical condition, by means of the keyboard 92. The computer 9 calculates a corneal ablation amount based on the inputted data to obtain the laser irradiation control data, and transmits the data to the control unit 50.

Further, into the computer 9, the operator inputs (sets) a desired pupil diameter of the eye E at the time of the laser irradiation (operation), and a permissible range taking the desired pupil diameter as a reference value. As the desired pupil diameter, the pupil diameter obtained by a corneal share measurement apparatus before the operation may be inputted, or a relatively larger pupil diameter may be inputted if the patient places greater importance to night vision. As the desired pupil diameter and the permissible range thereof, various ones are inputted depending on the operator, the surgical condition and the like. For example, assume that the desired pupil diameter is 4 mm, and the permissible range is ±0.5 mm to the desired pupil diameter. Incidentally, the permissible range ray be inputted by the operator together with the desired pupil diameter, or may be set by the apparatus based on the inputted desired pupil diameter. Besides, when the area of the pupil region is to be obtained, a desired pupil area and the permissible range thereof are inputted (set).

Upon completion of preparation for the operation, the arm unit 2 provided with an irradiation exit of the laser beam is placed above the eye E. Each of the light sources 41 and 42 is lit, and the eye E is fixated on the fixation lamp 26. At this point, illuminations in an operating room except those in the apparatus may be turned off so that the pupil of the eye E is not affected thereby. The operator observes the anterior-segment or the eye E through the microscope unit 3, and moves the observation optical unit 5 by operating the joystick 7 and the switch 60 until the entire pupil becomes identifiable. At this point, the control unit 50 controls to actuate the respective driving units 51, 52 and 53 based on the signals from the joystick 7 and the switch 60 to move the arm unit 2 in the X- and Y-directions, and the observation optical unit 5 in the Z-direction, respectively.

When the pupil of the eye E becomes identifiable and the operator pushes the switch 62, the control unit 50 controls to start detecting the pupil diameter based on the output signal from the CCD camera 33, and determine whether or not the pupil diameter of the eye E falls within the permissible range taking the desired pupil diameter as the reference value which is previously set. In a case where the detected pupil diameter does not fall within the permissible range, the alarm 55 sounds to inform the operator thereof. Also, a detection value of the pupil diameter and the desired pupil diameter (set reference value) are displayed (the permissible range may be further displayed) on the monitor 91. This display allows the operator to know whether the pupil diameter of the eye E becomes the desired pupil diameter or not. In a case where the manual mode is selected for the light intensity adjustment of the light source 41, the light intensity may be adjusted with the switch 63. Besides, a comparison result such as a difference between the detection value of the pupil diameter and the desired pupil diameter (set reference value) may be displayed, and also an instruction on an increase or a decrease in the light intensity may be displayed after a value of the increase or decrease in the light intensity is obtained from the comparison result.

Here, in a case where the automatic mode is selected by the switch 64 for the light intensity adjustment of the light source 41, the control unit 50 controls to adjust the light intensity of the light source 41 based on the detected pupil diameter. When the illumination light intensity of the light source 41 increases, the pupil contracts. To the contrary, when the illumination light intensity decreases, the pupil dilates. Therefore, when the detected pupil diameter is larger than an upper limit value of the permissible range, the illumination light intensity may be adjusted to increase. To the contrary, when the detected pupil diameter is smaller than a lower limit value of the permissible range, the illumination light intensity maybe adjusted to decrease. Incidentally, automatic adjustment of illumination light intensity may be performed until the detected pupil diameter reaches the desired pupil diameter, not until it falls within the permissible range.

When the detected pupil diameter comes to fall within the permissible range, the control unit 50 controls to inform the operator accordingly by means of the monitor 91 or the alarm 55. Next, the operator further operates the joystick 7 and the switch 60 to perform alignment in the X-, Y- and Z-directions so that an unillustrated reticle and the pupil have a predetermined relationship.

The present apparatus is made to be able to perform automatic alignment in the X- and Y-directions based on the detection of the pupil center position by the eyeball position detection system. The automatic alignment is actuated by setting the switch 61 ON, When the pupil center position becomes detectable by the eyeball position detection system, the control unit 50 controls the driving units 51 and 52 to move the arm unit 2 in the X- and Y-directions so that the reference optical axis L for the laser irradiation corresponds to the pupil center position.

By pushing the switch 62 after confirming the completion of the alignment, automatic tracking is actuated to move the arm unit 2 so that a reference position on the image-pickup element of the CCD camera 33 (the position of the reference optical axis L) corresponds to the pupil center position. The detected pupil center position is compared with the reference position at all times. When the eye E moves beyond a predetermined permissible range, the control unit 50 controls to move the arm unit 2 in the X- and Y-directions based on comparison information so that the pupil center position may fall within the permissible range of the reference position. Incidentally, it is not always necessary that the position of the reference optical axis L corresponds to the pupil center position. It is essential only to store a positional relationship between the position of the reference optical axis L and the pupil center position by pushing the switch 62 after the pupil center position is aligned to a desired state, and to maintain the positional relationship.

Pushing the switch 62 brings the laser source 10 to a state ready to emit the laser beam. When the operator depresses the foot switch 8, the control unit 50 controls the laser source 10 to emit the laser beam. The emitted laser beam is irradiated onto the cornea Ec for ablation.

Hereinafter, a brief description will be given on corrective surgery by means of the irradiation optical system in the present embodiment. In the case of ablating a myopic spherical component, the control unit 50 controls to limit the ablation region by the aperture unit 18, and sequentially move the mirror 13 to move (scan) the laser beam in a Gaussian distribution direction. Then, each time the laser beam finishes moving in one direction (one scan), the moving (scanning) direction of the laser beam is changed by rotation of the image rotator 15 (for example, three directions at intervals of 120°) to ablate the region limited by the aperture unit 18 approximately uniformly. By performing these processes each time the opening diameter of the aperture unit 18 is changed sequentially, the spherical component of the cornea Ec, which is deep in the center part and shallow in the peripheral part, may be ablated.

There is a case where the pupil changes also during the laser irradiation (during the operation) due to strain on the patient and the like. Therefore, the control unit 50 controls to continue the detection of the pupil diameter also during the laser irradiation. In a case where the detected pupil diameter deviates from the permissible range of the desired pupil diameter, the control unit 50 controls to stop the laser emission from the laser source 10 (stopping the laser emission includes also a case that a shutter is inserted into an optical path of the irradiation optical system). At the same time, the alarm 55 gives a warning to the operator. In a case where the automatic mode is selected for the light intensity adjustment, the control unit 50 controls to automatically adjust the light intensity of the light source 41. In a case where the automatic mode is not selected, the monitor 91 or the alarm informs the operator that the pupil diameter deviates from the permissible range, so that the operator manually adjusts the light intensity based on this information. When the pupil diameter falls within the permissible range, the laser irradiation is made ready again and the operator may resume the laser irradiation with the foot switch 8.

As described above, a deviation of the pupil center position which is the reference position of the alignment and the tracking at the time of the laser irradiation is reduced by bringing the pupil diameter of the patient's eye to be a desired length, so that the deviation of the irradiation position is also reduced.

Incidentally, if the pupil diameter does not fall within the permissible range even when the light intensity of the light source 41 is adjusted, the alarm 55 and the monitor 91 inform the operator accordingly. In this case, the operator may respond at his/her discretion, for example, by charging the desired pupil diameter, the permissible range thereof.

Various modifications may be applied to the above-described preferred embodiment. For example, instead of the light source 41 or observation which is used as illumination means for changing the pupil (iris) of the eye E, the fixation lamp 26 may be employed and the light intensity thereof may be adjusted.

Further, the irradiation optical system may include a mirror (two galvanometers or the like) which scans the laser beam formed into a small spot of 0.1-1.0 mm two-dimensionally in the X- and Y-directions. In this case, the irradiation position may be moved by driving and controlling the scanning mirror. In addition, in the case of the irradiation optical system which includes an aperture unit with a variable opening diameter for limiting the ablation region, the irradiation position may be moved by eccentrically moving an axis of the projecting lens which projects an opening of the aperture unit onto the cornea.

Furthermore, the present invention may apply to any apparatus which determines the irradiation position with reference to the position (part) relating to the pupil (iris), such as an apparatus which performs alignment of the irradiation position based on a contrast between the sclera and the iris (refer to Japanese Patent Application Unexamined Publication No. 2003-505178), and an apparatus which performs alignment of the irradiation position based on a mark previously provided on the eye (iris and the like) (refer to Japanese Patent Application Unexamined Publication No. 2003-511206).

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic laser irradiation apparatus comprising:
   an irradiation optical system for irradiating a laser beam onto a patient's eye;
   an illumination unit, including an illumination light source, in which light intensity of visible illumination light onto the eye is adjustable;
   a detection unit which detects at least one of a pupil area and a pupil diameter of the eye;
   a setting unit which sets a reference value of at least one of the pupil area and the pupil diameter, and a permissible range of the reference value; and
   an informing unit which informs at least one of a detection value of the detection unit with the set reference value and a comparison result between the detection value and the set reference value,
   wherein the informing unit informs at least one of that the detection value falls within the set permissible range, and that the detection value does not fall within the set permissible range.

2. An ophthalmic laser irradiation apparatus comprising:
   an irradiation optical system for irradiating a laser beam onto a patient's eye;
   an illumination unit, including an illumination light source, in which light intensity of visible illumination light onto the eye is adjustable;
   a detection unit which detects at least one of a pupil area and a pupil diameter of the eye;
   a setting unit which sets a reference value of at least one of the pupil area and the pupil diameter; and
   an informing unit which informs at least one of a detection value of the detection unit with the set reference value and a comparison result between the detection value and the reference value,
   wherein the informing unit informs an instruction on one of an increase and a decrease in the illumination light intensity based on the comparison result.

3. An ophthalmic laser irradiation apparatus comprising:
   an irradiation optical system for irradiating a laser beam onto a patient's eye;
   an illumination unit, including an illumination light source, in which light intensity of visible illumination light onto the eye is adjustable;
   a detection unit which detects at least one of a pupil area and a pupil diameter of the eye;
   a setting unit which sets a reference value of at least one of the pupil area and the pupil diameter; and
   a control unit which controls the illumination unit to adjust the light intensity of the visible illumination light so that a detection value of the detection unit becomes the set reference value.

4. The ophthalmic laser irradiation apparatus according to claim 3,
   wherein the setting unit sets the reference value of at least one of the pupil area and the pupil diameter, and a permissible range of the reference value, and
   the control unit adjusts the illumination light intensity so that the detection value falls within the set permissible range.

5. The ophthalmic laser irradiation apparatus according to claim 3, wherein the detection unit includes an image-pickup element, and detects at least one of a pupil edge and a pupil center.

6. An ophthalmic laser irradiation apparatus comprising:
   an irradiation optical system for irradiating a laser beam onto a patient's eye;
   an illumination unit, including an illumination light source, in which light intensity of visible illumination light onto the eye is adjustable;
   a detection unit which detects at least one of a pupil area and a pupil diameter of the eye;
   a setting unit which sets a reference value of at least one of the pupil area and the pupil diameter; and
   a control unit which judges whether a detection value of the detection unit becomes the set reference value, and controls laser irradiation based on a judgment result.

7. The ophthalmic laser irradiation apparatus according to claim 6,
   wherein the setting unit sets the reference value of at least one of the pupil area and the pupil diameter, and a permissible range of the reference value, and
   the control unit judges whether the detection value falls within the set permissible range.

8. The ophthalmic laser irradiation apparatus according to claim 6, wherein the detection unit includes an image pickup-element, and detects at least one of a pupil edge and a pupil center.

* * * * *